United States Patent
Hartung et al.

(10) Patent No.: US 7,197,106 B2
(45) Date of Patent: Mar. 27, 2007

(54) DETECTOR FOR A COMPUTED TOMOGRAPHY UNIT, AND A COMPUTED TOMOGRAPHY UNIT HAVING SUCH A DETECTOR

(75) Inventors: Andre Hartung, Duesseldorf (DE);
Rainer Raupach, Adelsdorf (DE);
Jens-Peter Scharnagl, Fuerth (DE);
Eberhard Ten Weges, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/252,767

(22) Filed: Oct. 19, 2005

(65) Prior Publication Data
US 2006/0126781 A1  Jun. 15, 2006

(30) Foreign Application Priority Data
Oct. 20, 2004 (DE) .................. 10 2004 051 172

(51) Int. Cl.
*G01N 23/08* (2006.01)
(52) U.S. Cl. ............................. 378/19; 378/4
(58) Field of Classification Search .............. 378/9, 378/19, 4, 17
See application file for complete search history.

(56) References Cited

U.S. PATENT DOCUMENTS

| 4,196,352 A | | 4/1980 | Berninger et al. | |
|---|---|---|---|---|
| 5,966,422 A | * | 10/1999 | Dafni et al. | ........... 378/9 |
| 6,041,097 A | | 3/2000 | Roos et al. | |
| 6,650,727 B2 | * | 11/2003 | Kuroda | ........... 378/19 |

FOREIGN PATENT DOCUMENTS

| DE | 29 16 848 A1 | 11/1979 |
|---|---|---|
| DE | 195 02 574 C2 | 9/1999 |

* cited by examiner

*Primary Examiner*—Edward J. Glick
*Assistant Examiner*—Hoon Song
(74) *Attorney, Agent, or Firm*—Harness, Dickey & Pierce

(57) ABSTRACT

A detector and a computed tomography unit are disclosed. The detector includes a first detector region for acquiring projections of a first projection direction, and additionally includes at least a second and a third detector region for acquiring projections of a second and a third projection direction. Given appropriate operation of the detector, it is possible to carry out flexible scanning of an examination area in an optional fashion with a high time resolution, a high volume coverage or with a large coverage of a cross section of the examination area, doing so perpendicular to the system axis of the computed tomography unit.

19 Claims, 2 Drawing Sheets

Figure 1:
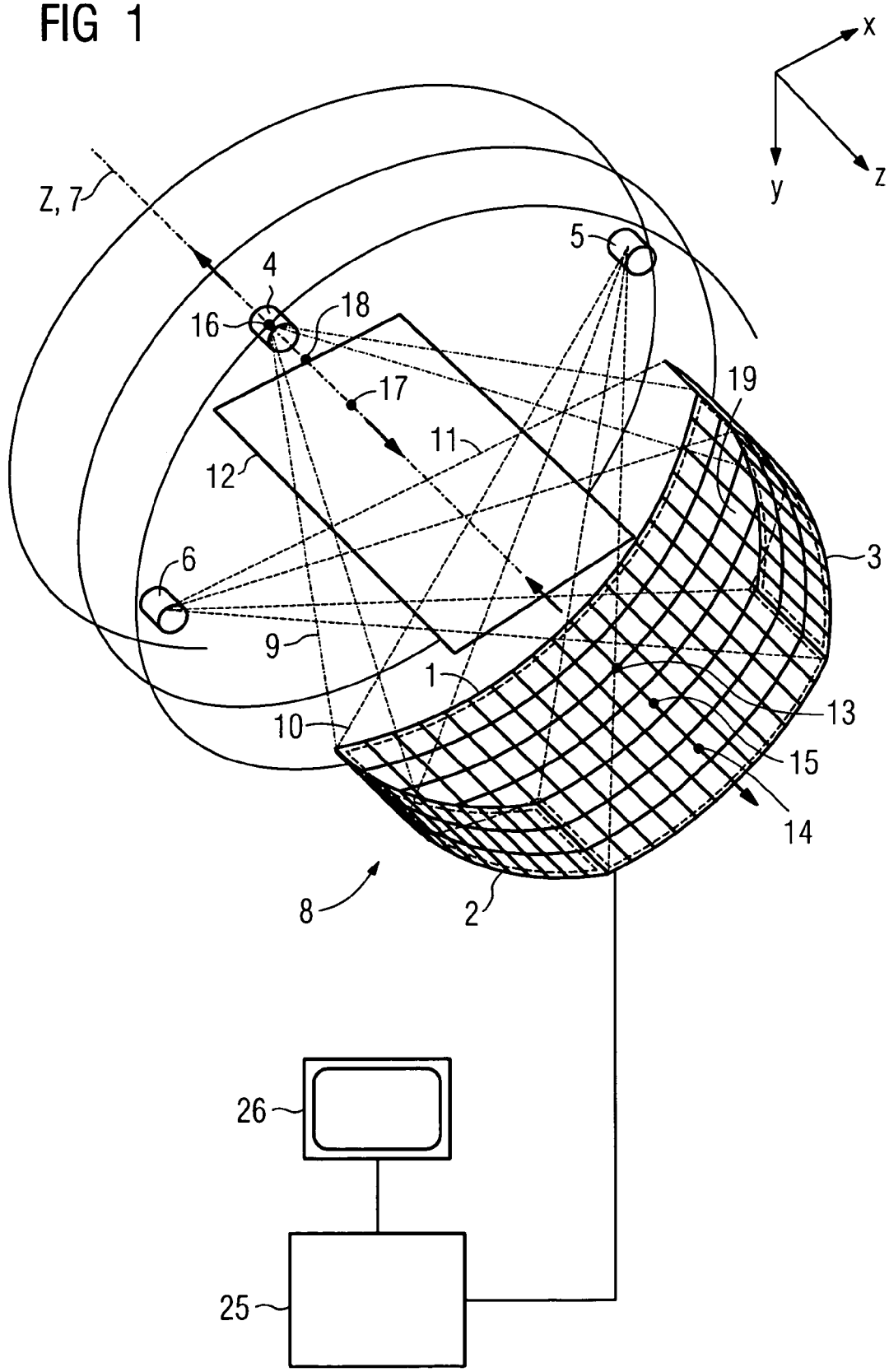

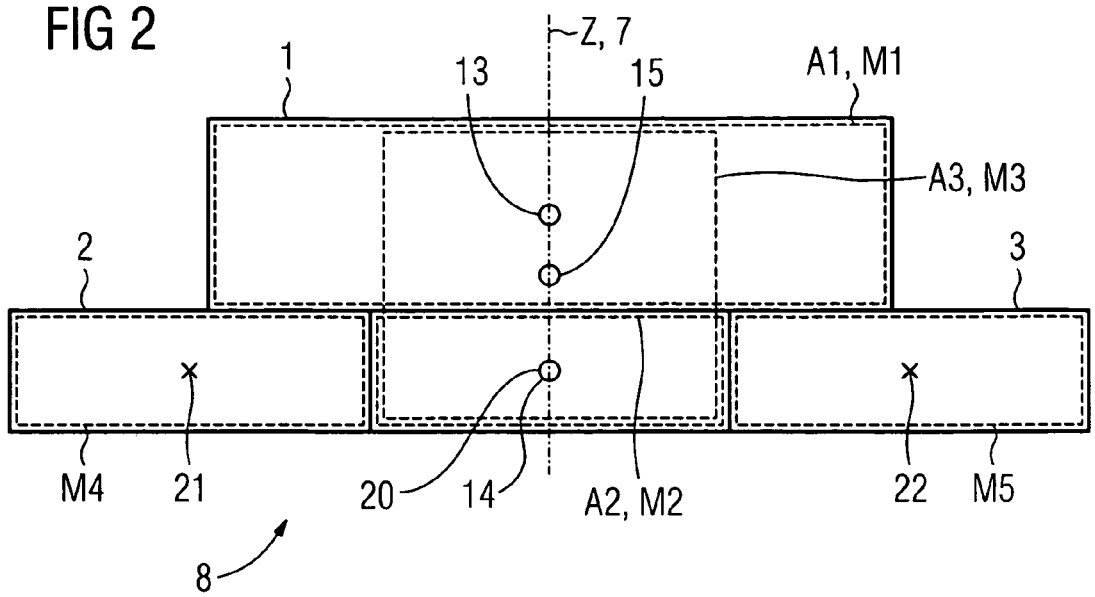
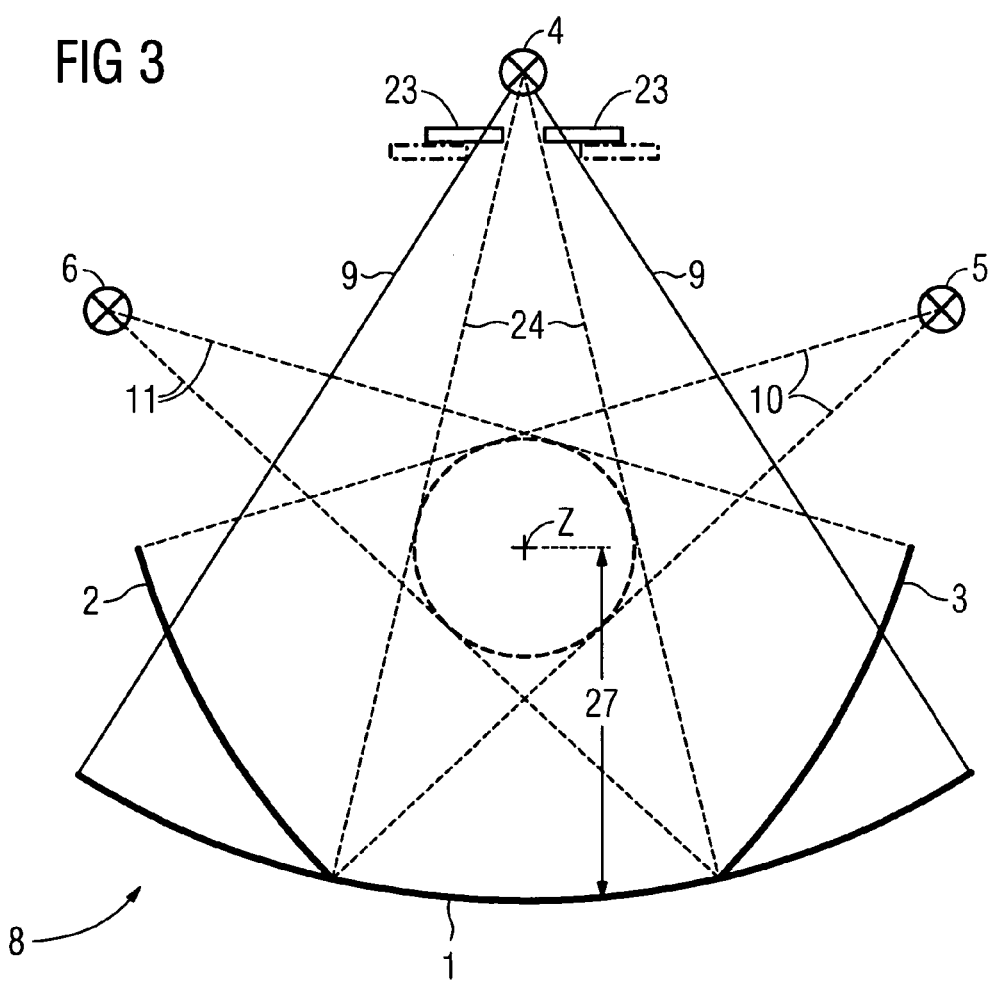

DETECTOR FOR A COMPUTED TOMOGRAPHY UNIT, AND A COMPUTED TOMOGRAPHY UNIT HAVING SUCH A DETECTOR

The present application hereby claims priority under 35 U.S.C. §119 on German patent application number DE 10 2004 051 172.1 filed Oct. 20, 2004, the entire contents of which is hereby incorporated herein by reference.

FIELD

The invention generally relates to a detector for a computed tomography unit. For example, it may relate to a computed tomography unit having such a detector.

BACKGROUND

A detector and a computed tomography unit having a detector are known for example from DE 195 02 574 C2. In the known case, the detector is of rectangular configuration and aligned in a fashion situated opposite an x-ray emitter such that an x-radiation emanating from a focus of the x-ray emitter strikes the measuring field of the detector.

Detector and x-ray emitter can be set rotating about a system axis of the computed tomography unit via a rotary frame. When the computed tomography unit is being operated, during a rotation of the recording system a multiplicity of projections of an examination area from different rotary angle positions and/or from different projection directions are acquired in temporal succession in this way by a detector, and a downstream processing stage is used to produce tomograms or voxels from them by calculation.

The dimension of the detector is typically adapted with regard to a specific field of application of examinations. A detector adapted for examining a heart has, for example, a large extent in the direction of the system axis of the computed tomography unit in order to cover a large volume and to suppress movement artifacts. In turn, a large extent of the detector transverse to the direction of the system axis is required in examining the interior of a patient's body.

Moreover, DE 29,16,848 A1 also discloses computed tomography units having a number of recording systems arranged separately from one another. Each recording system respectively includes a detector and an x-ray emitter which simultaneously acquire projections from two different projection directions. Such computed tomography units having a number of recording systems are used whenever the aim is to carry out scanning of the examination area with an increased scanning rate.

SUMMARY

An aim of at least one embodiment of the invention is to fashion a detector for a computed tomography unit, or a computed tomography unit in such a way that it is possible to scan an examination area in a simple and flexible way.

An object may be achieved via a detector.

According to at least one embodiment of the invention, the detector includes a first detector region for acquiring projections of a first projection direction, and additionally includes at least a second and a third detector region for acquiring projections of a second and a third projection direction.

The different detector regions of the only one detector can be operated in combination or else autonomously, and so an examination area can be scanned in a flexible way in accordance with the requirements. In the case of simultaneous operation of the detector regions, it is possible, for example, to carry out a simultaneous acquisition of projections from at least three different projection directions such that the scanning of the examination area can be performed with an increased time resolution or with an increased scanning rate. However, it is also possible for the first detector region to be operated autonomously and independently of the second and third detector regions. The following segmentations may be advantageously provided for the first detector region:

In a first advantageous refinement of at least one embodiment of the invention, the first detector region can be divided into two sections, the first section transverse to the longitudinal axis of the detector, which runs at least substantially parallel to the system axis of the computed tomography unit, having a greater extent than the second section.

Moreover, the first detector region can advantageously additionally be divided into a third section, the third section including the second section and a part of the first section in such a way that in its extent transverse to the longitudinal direction of the detector the third section corresponds substantially to the second section, and in the direction of the longitudinal axis of the detector it corresponds substantially to the sum of the extent of the first and second sections. The first detector region can be constructed in a simple way by means of conventional rectangular detector modules owing to this type of segmentation.

The first detector region preferably includes, in accordance with the divided sections, at least three measuring fields that can be operated independently of one another. The first measuring field may be assigned to the first section, the second measuring field may be assigned to the second section, and the third measuring field may be assigned to the third section. Differently dimensioned measuring fields permit scanning adapted to the object to be examined. The measuring fields may be formed directly from the sections. However, measuring fields that are smaller than the corresponding sections are also conceivable.

The first measuring field can be used autonomously, and, in particular, enables the scanning of objects with a large cross-sectional extent owing to the large extent of the surface of the measuring field transverse to the longitudinal axis of the detector by comparison with all the other measuring fields.

By contrast therewith, the second measuring field may be used, for example, in conjunction with the measuring field of the second and third detector regions such that an object can be scanned simultaneously from the three different projection directions. As already mentioned, in such an operation the scanning may be carried out with an increased time resolution or with an increased scanning rate. The second and the third detector regions expediently have substantially the same extent in the direction of the longitudinal axis and transverse to the direction of the longitudinal axis by comparison with the second section of the first detector region, such that the three different projection directions in each case exhibit a solid angle of the examination area to be covered that is at least essentially the same in magnitude. The second section of the first detector region may be advantageously arranged between the second and the third detector regions so that the scanning is performed at the same positions along the system axis of the computed tomography unit.

The second detector region and the third detector region may be angled away from the second section of the first detector region. X-ray emitter and assigned detector region are aligned relative to one another such that the fan-shaped x-radiation emanating from the respective x-ray emitter strikes the detector surface perpendicularly. For this purpose, the two detector regions and the second section of the first detector region are, for example, arranged at the same radius in a fashion perpendicular to the system axis of the computer tomography unit and have a curvature corresponding to a circle with this radius. Projections having the same imaging properties can be achieved whenever the focus of the respective x-ray emitter is arranged at the same distance from the system axis on the corresponding side situated opposite.

The third measurement area can be operated autonomously, in turn. The large extent of the third measuring field in the direction of the longitudinal axis of the detector by comparison with all the other measuring fields offers the advantage that it is possible to carry out scanning of objects with a large volume coverage. Movement artifacts owing to intrinsic object movements, such as occur during dynamic object examinations for example during perfusion, can thereby be avoided.

Advantageously, the detector can be set to a first position assigned to the first measuring field, to a second position assigned to the second measuring field, and to a third position assigned to the third measuring field in such a way that an x-radiation emanating from the x-ray emitter of the computed tomography unit illuminates the respective measuring field. The adjustment of the detector position, for example via a rail system provided therefore, can be carried out in a simple way and ensures central illumination of the respectively active measuring field.

An object may be achieved furthermore, via a computed tomography unit having a detector.

In an advantageous refinement of at least one embodiment of the invention, an illumination adapted to a measuring field can also be performed by adjusting the x-radiation of the first x-ray emitter. The adjustment of the x-radiation is possible in a simple way by displacing the first x-ray emitter which is, for example, mounted on rails, such that the x-radiation illuminates the first, the second and the third measuring fields centrally.

So that an unnecessary radiation burden of the object can be avoided, the x-radiation of the first x-ray emitter can advantageously be set to the respective measurement area via a diaphragm that can be set.

The recording system of the computer tomography unit may include, for example, a second and a third x-ray emitter, the second x-ray emitter being assigned to the second detector region, and the third x-ray emitter being assigned to the third detector region.

Other advantages and refinements of the invention will become apparent from the example embodiment explained below with reference to the appended drawings, in which:

FIG. 1 shows in a view that is partly a block diagram and partly perspective a computed tomography unit having a detector according to at least one embodiment of the invention, FIG. 2 shows the detector according to at least one embodiment of the invention from FIG. 1, in a plan view, and FIG. 3 shows the recording system of the computed tomography unit according to at least one embodiment of the invention from FIG. 1 in a side view, an adjustable diaphragm additionally being illustrated.

DETAILED DESCRIPTION OF THE EXAMPLE EMBODIMENTS

A computed tomography unit according to at least one embodiment of the invention is shown in FIG. 1 in an illustration that is partly perspective and partly in the form of a block diagram. The computed tomography unit essentially includes a recording system having a detector 8, provided according to at least one embodiment of the invention, and having three x-ray emitters 4, 5, 6 assigned to the detector, an arithmetic logic unit 25 and a display unit 26.

The detector 8 has three different detector regions 1, 2, 3. Each detector region 1 or 2 or 3 is respectively assigned an x-ray emitter 4 or 5 or 6 for acquiring projections of a specific projection direction. The first x-ray emitter 4 is assigned to the first detector region 1, the second x-ray emitter 5 is assigned to the second detector region 2, and the third x-ray emitter 6 is assigned to the third detector region 3. X-ray emitter 4, or 5 or 6 and detector region 1 or 2 or 3 are respectively arranged on a rotary frame (not illustrated) situated opposite one another in such a way that during operation of the computed tomography unit an x-ray beam emanating from a focus of the respective x-ray emitter 4 or 5 or 6 and bounded by the respective edge beams strikes the corresponding detector region 1 or 2 or 3. The x-ray emitters 4, 5, 6 are arranged in the direction of rotation of the rotary frame, which corresponds to a circumferential direction about the z-axis of a rectangular coordinate system shown in FIG. 1, at different positions along the rotary frame such that projections of an object supported on a bearing device 12 can be acquired by only one detector 8 from three different projection directions at the same time.

For the purpose of acquiring the projections, the detector 8 has in each detector region 1 or 2 or 3 detector elements 19 that are assigned to columns and to rows, only one thereof being provided with a reference numeral in the drawing. The detector 8 can, for example, operate according to the functional principle of a scintillation detector or of a directly converting semiconductor detector. In the context of the present document, x-ray emitters are understood as all x-ray sources that generate an x-radiation emanating from a focus. An x-ray emitter in this sense is, for example, an x-ray tube.

FIG. 2 shows the detector 8 according to at least one embodiment of the invention and having three different detector regions 1, 2, 3, in a plan view. The first detector region 1 has the shape of a t and can be divided geometrically into two sections A1, A2, in principle. Transverse to the longitudinal axis 7 of the detector 8, which runs at least substantially parallel to the z-axis of the rectangular coordinate system shown in FIG. 1, the first section A1 has a greater extent than the second section A2. A third geometrically possible section A3 results from the combination of the second section A2 with a part of the first section A1 such that, in its extent transverse to the longitudinal axis 7 of the detector 8, the third section A3 corresponds substantially to the second section A2, and in the direction of the longitudinal axis 7 of the detector 8 it corresponds substantially to the sum of the extent of the first and second sections A1, A2.

Each section A1 or A2 or A3 has a rectangular shape. One advantage of this segmentation results inter alia from the possibility of constructing the first detector region 1 via conventional rectangular detector modules, each section A1 or A2 or A3 being capable of containing a plurality of detector modules.

The two other detector regions 2, 3 are arranged with reference to the first detector region 1 such that the second section A2 of the first detector region 1 is positioned between the second and third detector regions 2, 3, and that the midpoints 20, 21, 22 of the surfaces of the second detector region, the third detector region and the second section A2 of the first detector region 1 align with one another in the transverse direction with reference to the longitudinal axis 7 of the detector 8.

The first detector region 1 can be operated such that three different measuring fields M1, M2, M3 can be used. The first measuring field M1 corresponds in this example to the first section A1, the second measuring field M2 corresponds to the second section A2 and the third measuring field M3 corresponds to the third section A3. It is also possible however, to conceive of more than three useful measuring fields, or measuring fields of other dimensions, or sections of the first detector region that are of different type. It is crucial merely that the respective measuring field acquire the projections of an examination region in the direction of the longitudinal axis, and in the transverse direction relative to the longitudinal axis of the detector in accordance with the requirements of an examination. The basic t shape of the first detector region 1 is merely only one of many possible embodiments.

The first measuring field M1 of the first detector region 1 can be operated autonomously, and by comparison with all the other measuring fields M2, M3, M4, M5, has a large extent in the transverse direction in relation to the longitudinal axis of the detector, and enables the acquisition of objects with a large cross-sectional extent. The first measuring field M1 is therefore suitable, for example, for examining the interior of a patient's body.

In contrast, the third measurement area M3 has a large extent in the direction of the longitudinal axis 7 of the detector 8 by comparison with all the other measurement areas M1, M2, M4, M5. The third measurement area M3 can likewise be operated autonomously and is suitable, in particular, for scanning objects in which acquiring projections in a fashion free from movement artifacts requires a large coverage of the volume in the direction of the longitudinal axis 7 of the detector 8. A high volume coverage is required, for example, for dynamic object examinations for example during perfusion.

The second measurement area M2 of the first detector region 1 can be used together with a respective measurement area of the second and of the third detector region M4, M5 such that each rotary angle position of the recording system projections of an examination area can be recorded simultaneously from three different projection directions. In the case of such an operation of the detector 8, the scanning is performed at a high scanning rate and with a high time resolution. So as to be able to process the raw data obtained from the various measurement areas M2, M4, M5 with one another in a simple way, the measuring field of the second and third detector regions M4, M5, and the second measuring field M2 of the first detector region 1 exhibit at least essentially the same dimensions.

By combining the first detector region 1 with the second and third detector regions 2, 3, the detector regions respectively being assigned to different directions of projection, the detector 8 can, as just stated, be used in a wide range of examinations of different type. Depending on the operation of the detector 8, it is optionally possible to carry out the scanning of an examination area with a high time resolution or a high volume coverage, or with a large coverage of a cross section perpendicular to the system axis of the computed tomography unit.

As shown in FIG. 1, detector 8 and first x-ray emitter 4 can be adjusted relative to one another such that the x-radiation can in each case be aligned centrally with the active measuring field M1 or M2 or M3 of the first detector region 1. The alignment of the x-radiation can be performed, for example, by adjusting the detector 8 in the direction of the z-axis to a first position 13, assigned to the first detector region 1 to a second position 14, assigned to the second detector region 2, and to a third position 15, assigned to the third detector region 3. As an alternative to the detector 8, it is also possible to adjust the first x-ray emitter 4 to three positions 16 and 17 and 18, respectively assigned to a detector region, in order to align the x-radiation. An adjustment can be undertaken in this case via a rail system assigned to the detector 8 or to the first x-ray emitter 4, for example.

It is expedient to provide for the purpose of positionally accurate adjustment positioning motors that can, for example, be driven via the arithmetic logic unit in accordance with user inputs. Given that the arithmetic logic unit is equipped with appropriate operating software, a user can select one of various operating modes before starting the examination. The arithmetic logic unit thereupon generates control signals in order to position the appropriate components so as to ensure illumination of the measuring field active for the examination.

FIG. 3 shows the recording system of the computed tomography unit according to at least one embodiment of the invention in a side view with a viewing direction in the direction of the z-axis, an adjustable diaphragm 23 assigned to the first x-ray emitter 4 being illustrated, in addition. The adjustable diaphragm 23 enables the fan-shaped x-radiation to be adapted to the respectively active measuring field M1 or M2 or M3 of the first detector region 1 so that, on the one hand, a complete illumination of the measuring field M1 or M2 or M3 is ensured and, on the other hand, an unnecessary radiation burden on the patient is avoided.

The first set opening, shown in FIG. 3, of the diaphragm 23 introduces the fan-shaped x-radiation bounded by the second edge beams 24 in such a way as to ensure that the second measurement area M2 of the first detector region 1 is completely illuminated. Given an appropriate position of the first x-ray emitter 4 relative to the detector 8, it is possible by adjusting the diaphragm 23 to a second opening indicated by dashes to introduce the x-radiation onto the first measuring field M1 completely and in a way restricted only to the required amount. The x-radiation introduced for the purpose of illuminating the first measuring field M1 is shown in FIG. 3 by the first edge beams 9.

It is expedient for the second and the third detector regions 2, 3, and the part of the first detector region 1 assigned to the second measuring field M2 to be arranged perpendicular to the z-axis at a distance 27 that is at least substantially the same such that the projections acquired by the appropriate measuring fields exhibit the same imaging properties.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following

The invention claimed is:

1. A detector for a computed tomography unit, comprising: a first detector region for acquiring projections of a first projection direction; and at least a second and a third detector region for acquiring projections of a second and a third projection direction, such that projections of an object are acquirable from three different projection directions at the same time, wherein the second and the third detector regions are angled away from the first detector region.

2. The detector as claimed in claim 1, wherein the first detector region is divisible into two sections, a first section transverse to the longitudinal axis of the detector, which runs at least substantially parallel to the system axis of the computed tomography unit, having a greater extent than the second section.

3. The detector as claimed in claim 2, wherein the first detector region is additionally divisible into a third section, the third section including the second section and a part of the first section in such a way that in its extent transverse to the longitudinal axis of the detector, the third section corresponds substantially to the second section, and in the direction of the longitudinal axis of the detector, the third section corresponds substantially to the sum of the extent of the first and second sections.

4. The detector as claimed in claim 2, wherein the second and third detector regions and the second section of the first detector region substantially have an identical extent in the direction of the longitudinal axis and transverse to the direction of the longitudinal axis.

5. The detector as claimed in claim 2, wherein the second section of the first detector region is arranged between the second and third detector regions, each of which has a measuring field.

6. The detector as claimed in claim 3, wherein the first detector region is operatable in such a way that at least first, second and third measuring fields are useable.

7. The detector as claimed in claim 6, wherein the first measuring field is assigned to the first section, the second measuring field is assigned to the second section, and the third measuring field is assigned to the third section.

8. The detector as claimed in claim 7, wherein the second measuring field of the first detector region is operatable together with the measuring field of the second detector region and the measuring field of the third detector region.

9. The detector as claimed in claim 6, wherein the detector is settable to a first position assigned to the first measuring field, to a second position assigned to the second measuring field, and to a third position assigned to the third measuring field, in such a way relative to the first x-ray emitter that x-radiation emanating from the first x-ray emitter illuminates the respective measuring field.

10. A computed tomography unit with a recording system arranged for rotation about a system axis, including a detector as claimed in claim 1 and at least a first x-ray emitter.

11. The computed tomography unit as claimed in claim 10, wherein the x-radiation of the first x-ray emitter is settable to a first, a second and third measuring field in such a way that the x-radiation illuminates the respective measuring field.

12. The computed tomography unit as claimed in claim 11, wherein the x-radiation is aligned by adjusting the first x-ray emitter.

13. The computed tomography unit as claimed in claim 10, wherein the x-radiation of the first x-ray emitter is aligned with the respective measurement area via a settable diaphragm.

14. The computed tomography unit as claimed in claim 10, wherein the recording system includes a second and a third x-ray emitter, the second x-ray emitter being assigned to the second detector region, and the third x-ray emitter being assigned to the third detector region.

15. The detector as claimed in claim 3, wherein the second and third detector regions and the second section of the first detector region substantially have an identical extent in the direction of the longitudinal axis and transverse to the direction of the longitudinal axis.

16. The detector as claimed in claim 3, wherein the second section of the first detector region is arranged between the second and third detector regions, each of which has a measuring field.

17. The detector as claimed in claim 2, wherein the first detector region is operatable in such a way that at least three measuring fields are useable.

18. A computed tomography unit with a recording system arranged in a fashion capable of rotation about a system axis, including a detector as claimed in claim 2 and at least a first x-ray emitter.

19. The detector as claimed in claim 1, wherein the first detector region has a T shape.

* * * * *